(12) United States Patent
Ahn et al.

(10) Patent No.: US 11,453,698 B2
(45) Date of Patent: Sep. 27, 2022

(54) PREPARATION METHOD OF VASCULAR LEAKAGE BLOCKERS WITH A HIGH YIELD

(71) Applicant: CURACLE CO., LTD., Seoul (KR)

(72) Inventors: Koo Hyeon Ahn, Seoul (KR); Myung-Hwa Kim, Seoul (KR); Jung-Ln Pyo, Seoul (KR); Chul Su Baek, Seoul (KR); Sung Hwan Kim, Seoul (KR)

(73) Assignee: CURACLE CO., LTD., Seoul (KR)

( * ) Notice: Subject to any disclaimer, the term of this patent is extended or adjusted under 35 U.S.C. 154(b) by 0 days.

(21) Appl. No.: 17/058,518

(22) PCT Filed: Jul. 28, 2020

(86) PCT No.: PCT/KR2020/009908
§ 371 (c)(1),
(2) Date: Sep. 1, 2021

(87) PCT Pub. No.: WO2021/118003
PCT Pub. Date: Jun. 17, 2021

(65) Prior Publication Data
US 2021/0395297 A1    Dec. 23, 2021

(30) Foreign Application Priority Data

Dec. 13, 2019  (KR) ........................ 10-2019-0166864

(51) Int. Cl.
*C07J 75/00*   (2006.01)
*C07J 17/00*   (2006.01)

(52) U.S. Cl.
CPC ............. *C07J 75/00* (2013.01); *C07J 17/005* (2013.01)

(58) Field of Classification Search
CPC ........... C07J 75/00; C07J 17/005; C07J 9/005
See application file for complete search history.

(56) References Cited

U.S. PATENT DOCUMENTS

| 2012/0245110 | A1 | 9/2012 | Kwon et al. |
| 2014/0378399 | A1 | 12/2014 | Kwon et al. |
| 2018/0289727 | A1 | 10/2018 | Kang et al. |

FOREIGN PATENT DOCUMENTS

| CN | 1073179 A | 6/1993 |
| CN | 102656153 A | 9/2012 |
| CN | 107073023 A | 8/2017 |
| EP | 2495242 A2 | 9/2012 |
| KR | 10-2011-0047170 A | 5/2011 |
| KR | 10-1481709 B1 | 2/2015 |
| KR | 10-2124470 B1 | 6/2020 |
| WO | 97/42215 A1 | 11/1997 |

*Primary Examiner* — Barbara P Badio
(74) *Attorney, Agent, or Firm* — Workman Nydegger

(57) ABSTRACT

The present invention relates to a preparation method of a novel vascular leakage blocker with a high yield. The preparation method is easy to react and more productive and economical than the conventional method by using an intermediate that can easily remove impurities generated during the reaction. In addition, the preparation method can produce a novel vascular leakage blocker with a high yield by using a new reagent that has not been previously used in the step of generating an isomer, and is very advantageous in producing a high-quality active pharmaceutical ingredient.

12 Claims, No Drawings

PREPARATION METHOD OF VASCULAR LEAKAGE BLOCKERS WITH A HIGH YIELD

This patent application is the National Stage of International Application No. PCT/KR2020/009908 filed Jul. 28, 2020, entitled "PREPARATION METHOD OF VASCULAR LEAKAGE BLOCKERS WITH A HIGH YIELD", which patent application, claims the benefit of and priority to Korean Application No. 10-2019-0166864, filed Dec. 13, 2019, the entire contents of these applications are herein incorporated by reference in their entirety.

BACKGROUND OF THE INVENTION

1. Field of the Invention

The present invention relates to a preparation method of a novel vascular leakage blocker with a high yield.

2. Description of the Related Art

The compound of formula 1-1 below has the compound name (E)-methyl 6-((3S, 8S, 9S, 10R, 13S, 14S, 17R)-3-(((5S, 6R)-5-acetoxy-6-(acetoxymethyl)-5,6-dihydro-2H-pyran-2-yl)oxy)-10,13-dimethyl-2, 3, 4, 7, 8, 9, 10, 11, 12, 13, 14, 15, 16,17-tetradecahydro-1H-cyclopenta[a]phenanthrene-17-yl)hept-5-enoate, and is a compound disclosed in Korean Patent Publication No. 10-2011-0047170 under the code name SAC-1004.

[Formula 1-1]

The above compound inhibits the apoptosis of vascular endothelial cells, suppresses the formation of actin stress fibers induced by VEGF, enhances the structure of cortical actin ring, and improves the stability of TJ (tight junction) between vascular cells, thereby inhibiting vascular leakage. In addition, the compound is known to be useful in preventing or treating various diseases caused by vascular leakage because it has excellent activity to not only inhibit the permeability of blood vessels but also restore the integrity of damaged blood vessels.

A preparation method of the compound of formula 1-1 is disclosed in Korean Patent Publication No. 10-2011-0047170. Particularly, as shown in reaction formula 1A below, it is disclosed that the compound can be prepared by the following procedure: protecting —OH with THP (tetrahydropyran) (step 1); performing Wittig reaction to form an alkenyl bond (step 2); alkylating through esterification (step 3); performing deprotection of THP (step 4); and preparing the final compound through glycosylation (step 5).

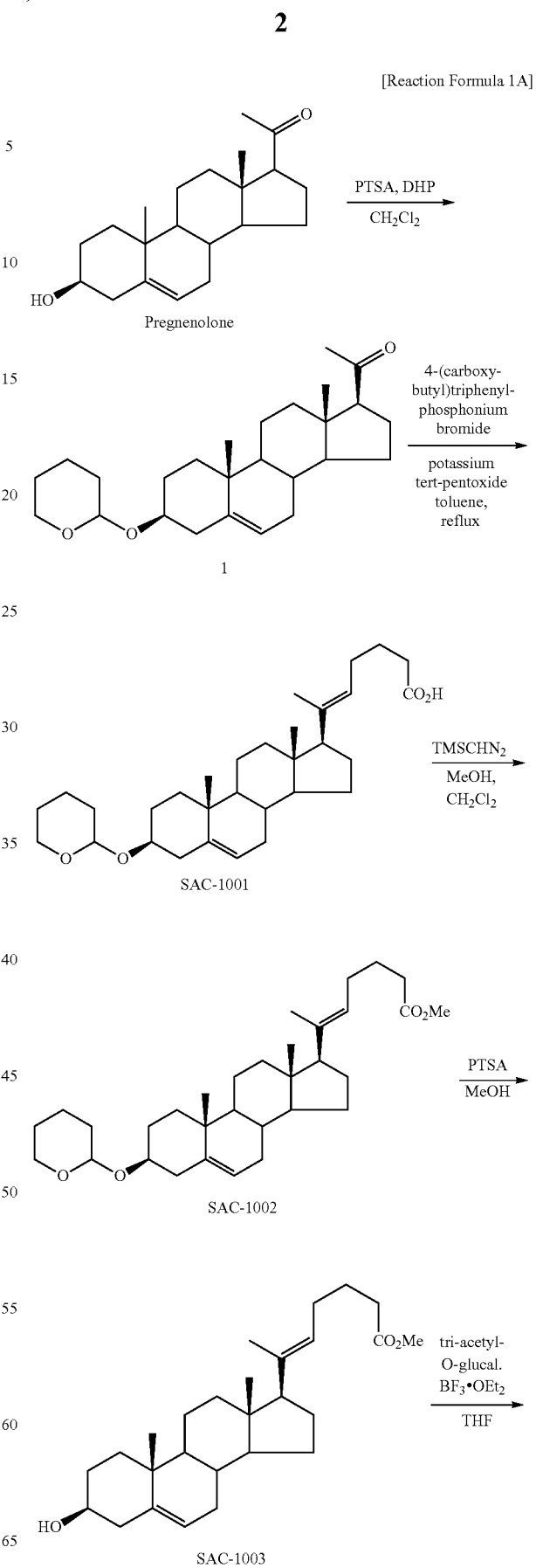

[Reaction Formula 1A]

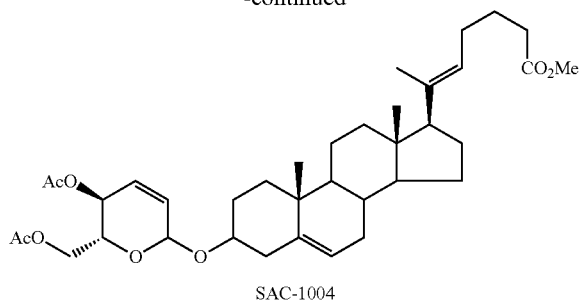

SAC-1004

The above preparation method has a problem of poor yield because the purification is performed by column chromatography. In addition, the separation, structure determination and mass production of stereoisomers have not been disclosed in the preparation method of the compound of formula 1-1.

Thus, it is necessary to develop a chemical preparation method for producing the compound with a high yield while enabling the separation and mass production of stereoisomers in the production of a high-quality active pharmaceutical ingredient.

SUMMARY OF THE INVENTION

It is an object of the present invention to provide a preparation method of a novel vascular leakage blocker with a high yield.

It is another object of the present invention to provide a mass production method of a novel vascular leakage blocker with a high yield.

To achieve the above objects, in an aspect of the present invention, the present invention provides a preparation method of a novel vascular leakage blocker represented by formula 1 comprising the following steps, as shown in reaction formula 1 below:

preparing a compound represented by formula 2 by reacting a compound represented by formula 4 with a compound represented by formula 5 (step 1); and preparing a compound represented by formula 1 by reacting the compound represented by formula 2 obtained in step 1 above with a compound represented by formula 3 in the presence of a catalyst (step 2).

[Reaction Formula 1]

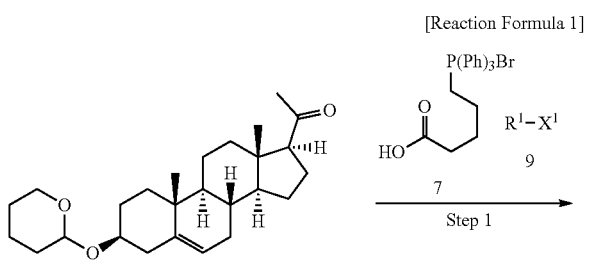

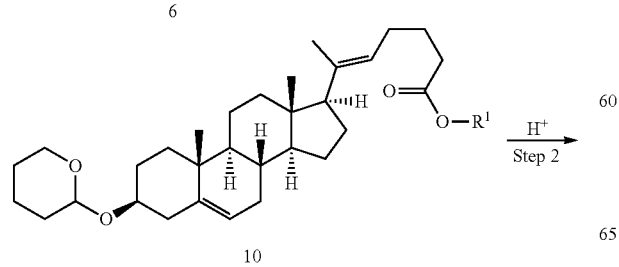

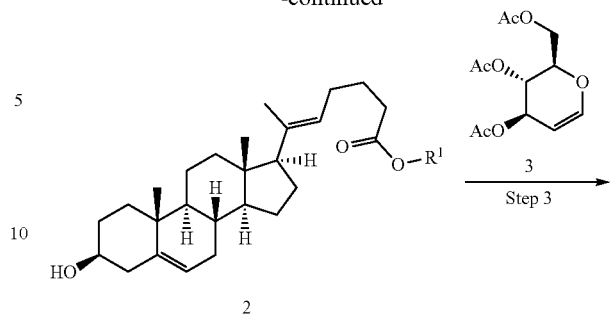

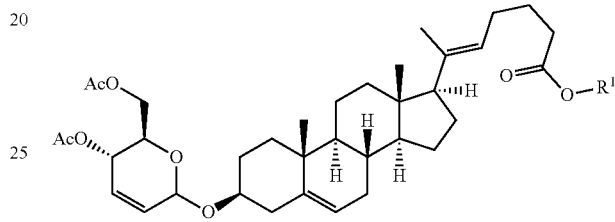

In reaction formula 1, $R^1$ is straight or branched $C_{1-10}$ alkyl.

In another aspect of the present invention, the present invention provides a preparation method of a novel vascular leakage blocker represented by formula 1 comprising the following steps, as shown in reaction formula 3 below:

preparing a compound represented by formula 6 by reacting pregnenolone with a compound represented by formula 8 (step 1);

preparing a compound represented by formula 4 by reacting the compound represented by formula 6 obtained in step 1 above with a compound represented by formula 1 (step 2);

preparing a compound represented by formula 2 by reacting the compound represented by formula 4 obtained in step 2 above with a compound represented by formula 5 (step 3); and preparing a compound represented by formula 1 by reacting the compound represented by formula 2 obtained in step 3 above with a compound represented by formula 3 in the presence of a catalyst (step 4).

[Reaction Formula 3]

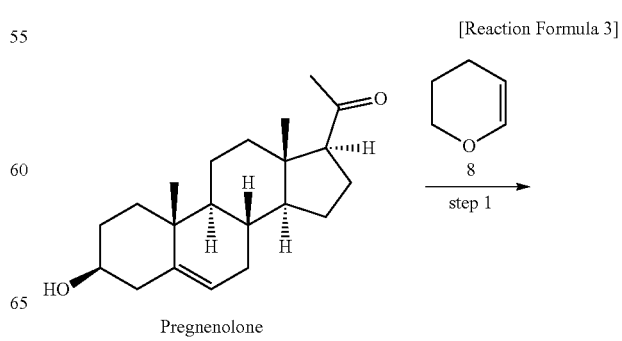

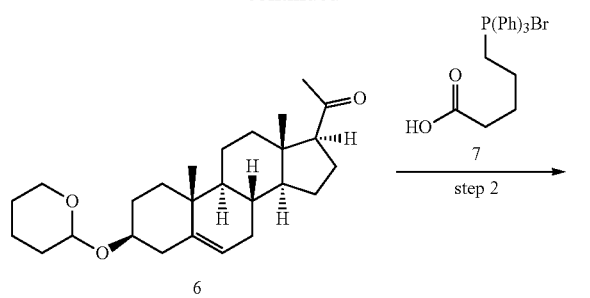

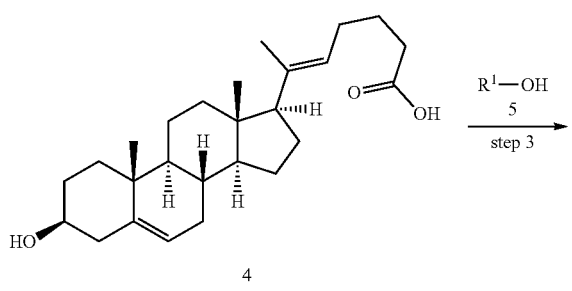

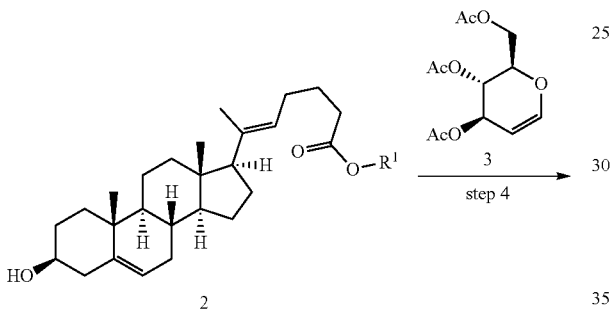

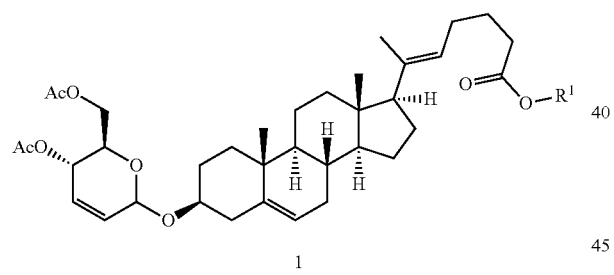

In reaction formula 3, $R^1$ is straight or branched $C_{1-10}$ alkyl.

In another aspect of the present invention, the present invention provides a preparation method of a novel vascular leakage blocker represented by formula 1 comprising the following steps, as shown in reaction formula 4 below:

preparing a compound represented by formula 10 by reacting a compound represented by formula 6, a compound represented by formula 7 and a compound represented by formula 9 (step 1);

preparing a compound represented by formula 2 by reacting the compound represented by formula 10 obtained in step 1 above with an acid material (step 2); and preparing a compound represented by formula 1 by reacting the compound represented by formula 2 obtained in step 2 above with a compound represented by formula 3 in the presence of a catalyst (step 3):

[Reaction Formula 4]

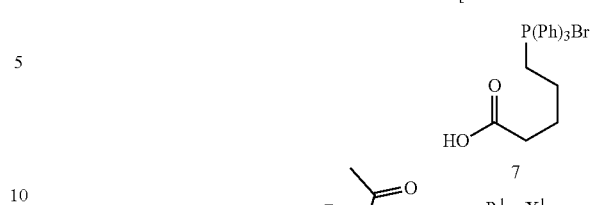

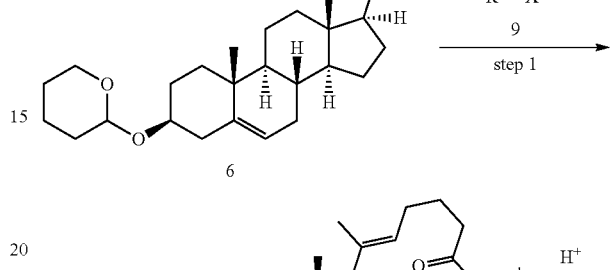

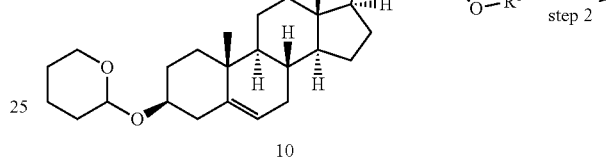

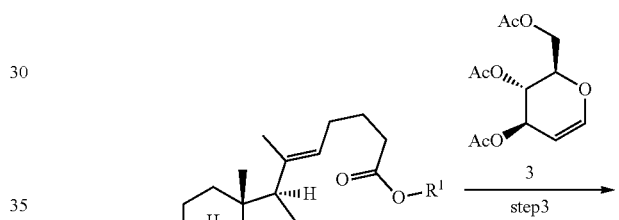

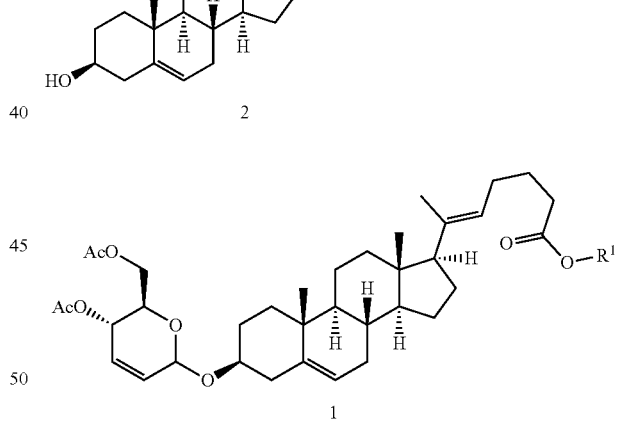

In reaction formula 4, $R^1$ is straight or branched $C_{1-10}$ alkyl; and $X^1$ is halogen.

In another aspect of the present invention, the present invention provides a mass production method of a novel vascular leakage blocker represented by formula 1 comprising a step of performing the preparation method of reaction formula 1 or the preparation method of reaction formula 3.

In another aspect of the present invention, the present invention provides a compound represented by formula 4, which is an intermediate produced in the process of preparing the compound represented by formula 1.

[Formula 4]

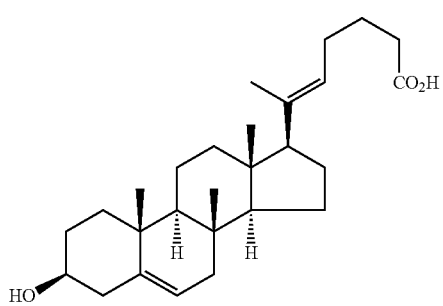

Advantageous Effect

The preparation method of the present invention is easy to react and more productive and economical than the conventional method by using an intermediate that can easily remove impurities generated during the reaction. In addition, the preparation method can produce a novel vascular leakage blocker with a high yield by using a new reagent that has not been previously used in the step of generating an isomer, and is very advantageous in producing a high-quality active pharmaceutical ingredient.

DESCRIPTION OF THE PREFERRED EMBODIMENTS

Hereinafter, the present invention is described in detail.

In an aspect of the present invention, the present invention provides a preparation method of a novel vascular leakage blocker represented by formula 1 comprising the following steps, as shown in reaction formula 1 below:

preparing a compound represented by formula 2 by reacting a compound represented by formula 4 with a compound represented by formula 5 (step 1); and preparing a compound represented by formula 1 by reacting the compound represented by formula 2 obtained in step 1 above with a compound represented by formula 3 in the presence of a catalyst (step 2).

[Reaction Formula 1]

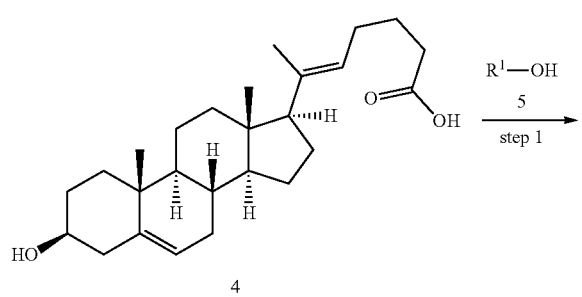

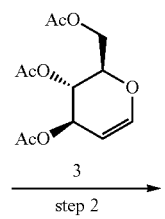

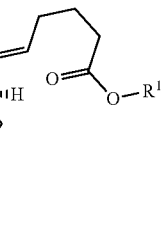

In reaction formula 1,
$R^1$ is straight or branched $C_{1-10}$ alkyl.
In reaction formula 1, $R^1$ can be straight or branched $C_{1-5}$ alkyl, straight or branched $C_{1-3}$ alkyl, or methyl.

Hereinafter, the preparation method represented by reaction formula 1 is described in detail.

Step 1 is to prepare an ester compound represented by formula 2 by reacting a carboxylic acid of a compound represented by formula 4 with an alcohol compound represented by formula 5. In this step, by using sulfuric acid as a catalyst in a methanol solvent, the preparation process is safer, simpler, and economical than using conventional methane.

Step 1 can be performed in the presence of an organic solvent selected from the group consisting of a non-polar solvent selected from the group consisting of hexane, benzene, toluene, 1,4-dioxane, chloroform, diethyl ether ($Et_2O$), tert-butyl methyl ether and dichloromethane (DCM); and a polar aprotic solvent selected from the group consisting of N-methylpyrrolidone, tetrahydrofuran (THF), ethyl acetate (EtOAc), acetone, dimethylformamide (DMF), acetonitrile (MeCN), dimethyl sulfoxide (DMSO) and propylene carbonate (PC), or a mixed solvent thereof, but not always limited thereto. In an embodiment of the present invention, methanol was used, but this is only an example and is not limited thereto.

In addition, step 1 can be performed at 0-80° C., and preferably can be performed at 50-80° C. In an embodiment of the present invention, step 1 was performed at 80° C., but this is only an example and is not limited thereto.

Further, the reaction time of step 1 can be 1 hour to 5 hours, and preferably can be 2 hours to 4 hours. In an embodiment of the present invention, the reaction was performed for 3 hours.

The reaction temperature and reaction time can be appropriately adjusted according to the type of substituents and the progress of the reaction.

Step 2 is to prepare a novel vascular leakage blocker compound represented by formula 1, the final target compound, by reacting alcohol of the ester compound represented by formula 2 prepared in step 1 above with tri-O- acetyl D-glucal represented by formula 3 in the presence of a catalyst. In this step, the yield was improved and the production of β-isomer was reduced.

The reaction catalyst can be any one selected from the group consisting of cation perfluoro-1-alkylsulfonate (The cation is lithium, sodium, potassium or cesium, alkyl is straight or branched perfluoro $C_{1-10}$ alkyl), (s)-camphor sulfonic acid, iodine, Amberlyst 15 and borontrifluoride etherate, or a mixture thereof, but not always limited thereto. In an embodiment of the present invention, a mixture of lithium nonafluoro-1-butylsulfonate (Li—NFBS) and (s)-camphor sulfonic acid was used, but this is only an example and is not limited thereto.

Step 2 can be performed in the presence of an organic solvent selected from the group consisting of a non-polar solvent selected from the group consisting of hexane, benzene, toluene, 1,4-dioxane, chloroform, diethyl ether ($Et_2O$), tert-butyl methyl ether and dichloromethane (DCM); and a polar aprotic solvent selected from the group consisting of N-methylpyrrolidone, tetrahydrofuran (THF), ethyl acetate (EtOAc), acetone, dimethylformamide (DMF), acetonitrile (MeCN), dimethyl sulfoxide (DMSO) and propylene carbonate (PC), or a mixed solvent thereof, but not always limited thereto.

In addition, step 2 can be performed at 0-80° C., preferably can be performed at 10-50° C., and more preferably can be performed at 30-40° C. In an embodiment of the present invention, step 2 was performed at 30-35° C., but this is only an example and is not limited thereto.

Further, the reaction time of step 2 can be 30 minutes to 5 hours, and preferably can be 1 hour to 3 hours. In an embodiment of the present invention, the reaction was performed for 2 hours.

The reaction temperature and reaction time can be appropriately adjusted according to the type of substituents and the progress of the reaction.

The compound represented by formula 2 of step 1 can be purified by recrystallization.

The recrystallization can be performed using any one selected from the group consisting of methanol, ethanol, toluene, ethyl acetate, acetonitrile and petroleum ether, or a mixed solvent thereof as a recrystallization solvent.

More preferably, the compound represented by formula 2 of step 1 can be recrystallized using methanol as a recrystallization solvent.

At this time, the recrystallization can be performed in a temperature range of 0° C. to 25° C., but this is only an example and is not limited thereto.

In the preparation method of reaction formula 1, the compound represented by formula 4, a starting material, can be prepared according to the preparation method comprising the following steps, as shown in reaction formula 2 below:

preparing a compound represented by formula 6 by reacting pregnenolone with a compound represented by formula 8 (step 1); and preparing a compound represented by formula 4 by reacting the compound represented by formula 6 obtained in step 1 above and a compound represented by formula 7 (step 2).

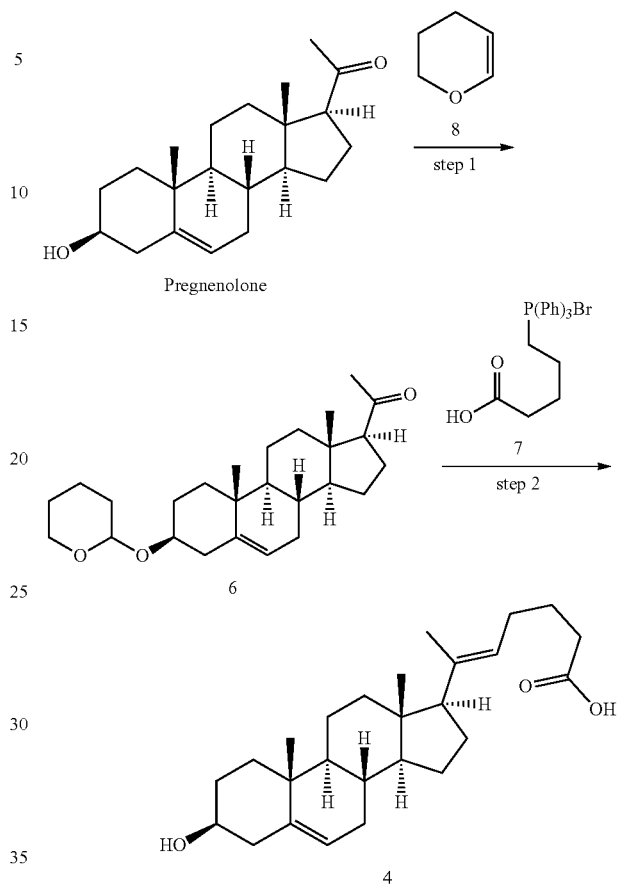

[Reaction Formula 2]

Hereinafter, the preparation method represented by reaction formula 2 is described in detail.

Step 1 is a step of protecting the alcohol group of pregnenolone with THP using a compound represented by formula 8, which is a well-known alcohol protection method, and can be performed by an informed method. In the present invention, p-toluenesulfonic acid monohydrate was used as a catalyst, but this is only an example and is not limited thereto.

Step 1 can be performed in the presence of an organic solvent selected from the group consisting of a non-polar solvent selected from the group consisting of hexane, benzene, toluene, 1,4-dioxane, chloroform, diethyl ether (Et:O), tert-butyl methyl ether and dichloromethane (DCM); and a polar aprotic solvent selected from the group consisting of N-methylpyrrolidone, tetrahydrofuran (THF), ethyl acetate (EtOAc), acetone, dimethylformamide (DMF), acetonitrile (MeCN), dimethyl sulfoxide (DMSO) and propylene carbonate (PC), or a mixed solvent thereof, but not always limited thereto. In an embodiment of the present invention, dichloromethane was used, but this is only an example and is not limited thereto.

In addition, step 1 can be performed at 0-50° C., and preferably can be performed at 0-5° C. In an embodiment of the present invention, step 1 was performed at 0° C., but this is only an example and is not limited thereto.

Further, the reaction time of step 1 can be 30 minutes to 5 hours, and preferably can be 1 hour to 3 hours. In an embodiment of the present invention, the reaction was performed for 2 hours.

The reaction temperature and reaction time can be appropriately adjusted according to the type of substituents and the progress of the reaction.

Step 2 is a step in which alkenyl carboxylic acid is introduced by reacting acetyl of pregnenolone with an alcohol group protected with THP represented by formula 6, prepared in step 1 above, with triphenyl phosphonium bromide of the compound represented by formula 7. In this step, after the introduction of alkenyl carboxylic acid, only the reaction solvent is removed (distillation under reduced pressure) without undergoing a separate purification process, and then the reaction of deprotecting the THP protecting group is immediately performed. The deprotection method can be performed by an informed method capable of removing THP, and as an example, the reaction can be performed under acid conditions.

In step 2, the introduction of alkenyl carboxylic acid can be performed in the presence of an organic solvent selected from the group consisting of a non-polar solvent selected from the group consisting of hexane, benzene, toluene, 1,4-dioxane, chloroform, diethyl ether ($Et_2O$), tert-butyl methyl ether and dichloromethane (DCM); and a polar aprotic solvent selected from the group consisting of N-methylpyrrolidone, tetrahydrofuran (THF), ethyl acetate (EtOAc), acetone, dimethylformamide (DMF), acetonitrile (MeCN), dimethyl sulfoxide (DMSO) and propylene carbonate (PC), or a mixed solvent thereof, but not always limited thereto. In an embodiment of the present invention, a mixed solvent of toluene and tetrahydrofuran was used, but this is only an example and is not limited thereto.

In addition, in an embodiment of the present invention, acetonitrile was used in the THP deprotection reaction of step 2, but this is only an example and is not limited thereto.

The alkenyl carboxylic acid introduction reaction in step 2 is a heating reaction, and can be performed at an external temperature of 100-130° C., and preferably at 115-125° C. In an embodiment of the present invention, the reaction was performed at 119° C., but this is only an example and is not limited thereto. The internal temperature is a temperature range that can maintain a mild reflux state.

Further, the reaction time for the introduction of alkenyl carboxylic acid in step 2 can be 1 to 30 hours, and preferably can be 10 to 24 hours. In an embodiment of the present invention, the reaction was performed for 22 hours, but this is only an example and is not limited thereto.

In an embodiment of the present invention, the THP deprotection reaction in step 2 can be performed at room temperature, or can be heated depending on the progress of the reaction.

In addition, the reaction time for the THP deprotection in step 2 can be 1 to 30 hours, and preferably can be 10 to 24 hours. In an embodiment of the present invention, the reaction was performed for 18 hours, but this is only an example and is not limited thereto.

The reaction temperature and reaction time can be appropriately adjusted according to the type of substituents and the progress of the reaction.

The compound represented by formula 6 of step 1 or the compound represented by formula 4 of step 2 can be purified by recrystallization.

The recrystallization can be performed using any one selected from the group consisting of methanol, ethanol, toluene, ethyl acetate, acetonitrile and petroleum ether, or a mixed solvent thereof as a recrystallization solvent, and a small amount of triethylamine (TEA) or the like can be added to the solvent to secure the stability of the compound.

More preferably, the compound represented by formula 6 of step 1 can be recrystallized using methanol as a recrystallization solvent and adding a small amount of TEA.

In addition, the compound represented by formula 4 of step 2 can be recrystallized using methanol as a recrystallization solvent.

At this time, the recrystallization can be performed in a temperature range of 0° C. to 25° C., but this is only an example and is not limited thereto.

In another aspect of the present invention, the present invention provides a preparation method of a novel vascular leakage blocker represented by formula 1 comprising the following steps, as shown in reaction formula 3 below:

preparing a compound represented by formula 6 by reacting pregnenolone with a compound represented by formula 8 (step 1);

preparing a compound represented by formula 4 by reacting the compound represented by formula 6 obtained in step 1 above with a compound represented by formula 7 (step 2);

preparing a compound represented by formula 2 by reacting the compound represented by formula 4 obtained in step 2 above with a compound represented by formula 5 (step 3); and preparing a compound represented by formula 1 by reacting the compound represented by formula 2 obtained in step 3 above with a compound represented by formula 3 in the presence of a catalyst (step 4).

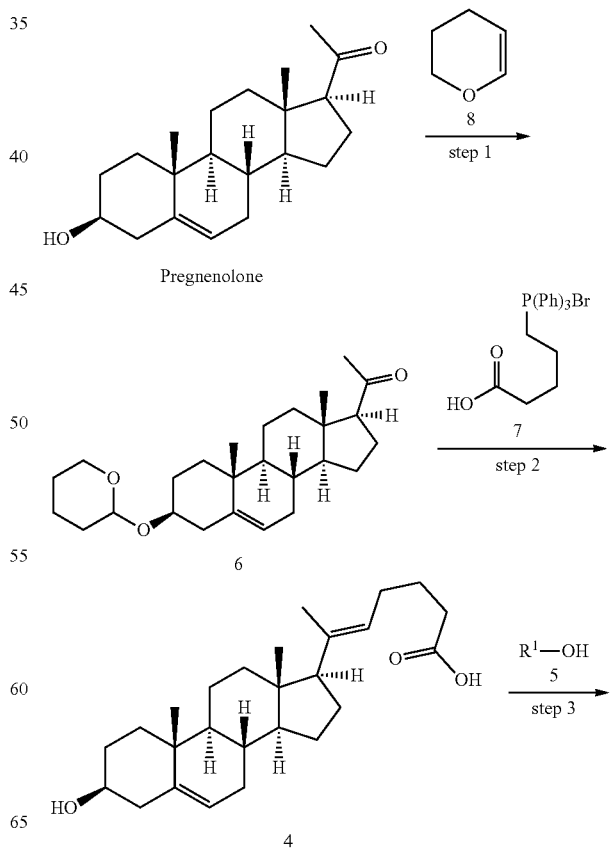

[Reaction Formula 3]

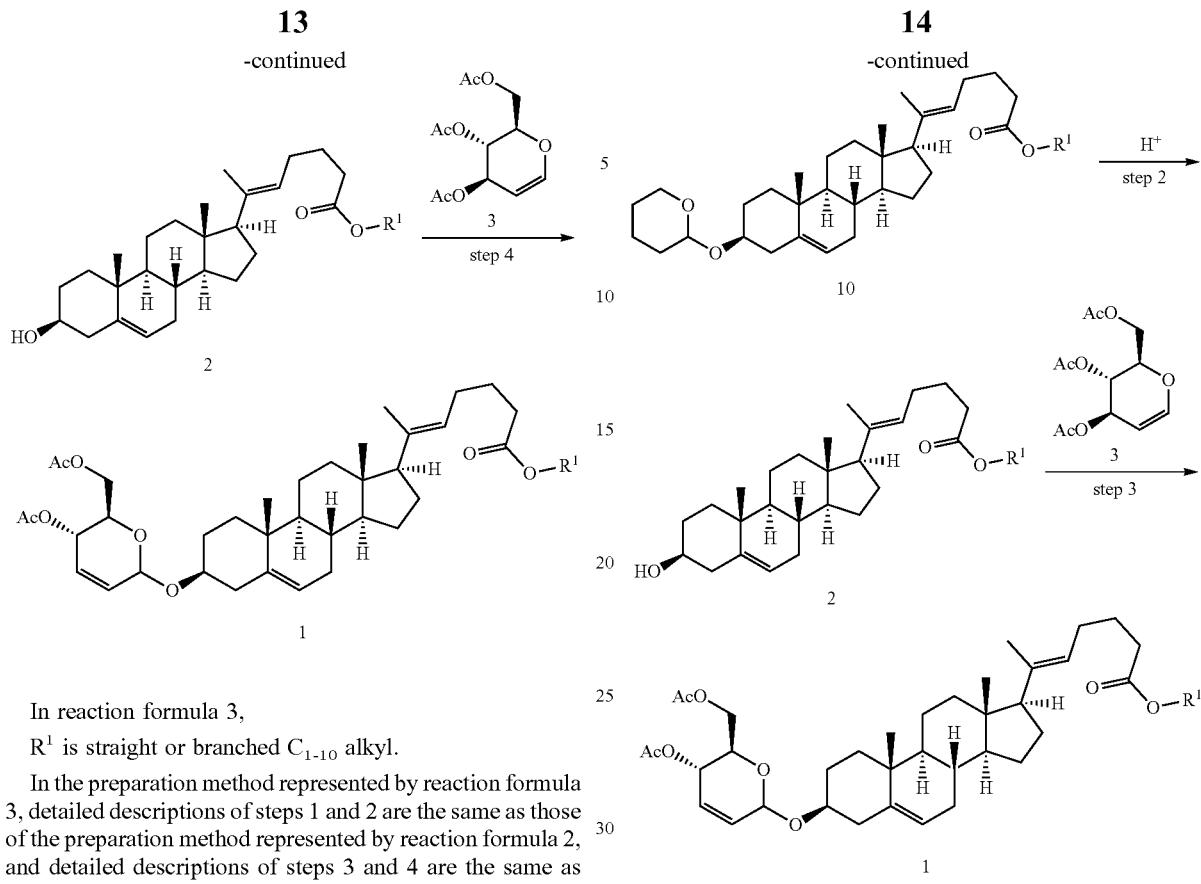

In reaction formula 3, $R^1$ is straight or branched $C_{1-10}$ alkyl.

In the preparation method represented by reaction formula 3, detailed descriptions of steps 1 and 2 are the same as those of the preparation method represented by reaction formula 2, and detailed descriptions of steps 3 and 4 are the same as those of the preparation method represented by reaction formula 1.

In another aspect of the present invention, the present invention provides a preparation method of a novel vascular leakage blocker represented by formula 1 comprising the following steps, as shown in reaction formula 4 below:

preparing a compound represented by formula 10 by reacting a compound represented by formula 6, a compound represented by formula 7 and a compound represented by formula 9 (step 1);

preparing a compound represented by formula 2 by reacting the compound represented by formula 10 obtained in step 1 above with an acid material (step 2); and preparing a compound represented by formula 1 by reacting the compound represented by formula 2 obtained in step 2 above with a compound represented by formula 3 in the presence of a catalyst (step 3).

[Reaction Formula 4]

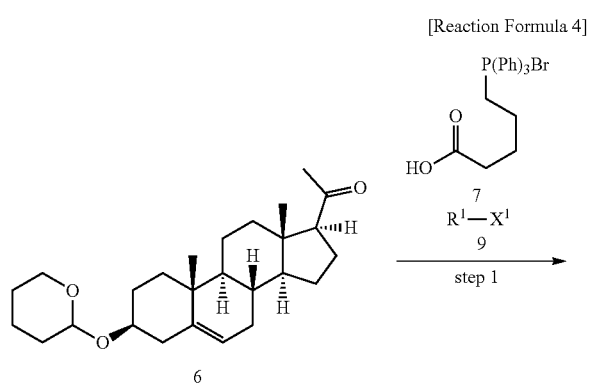

In reaction formula 4,
$R^1$ is straight or branched $C_{1-10}$ alkyl; and
$X^1$ is halogen.

Hereinafter, the preparation method represented by reaction formula 4 is described in detail.

Step 1 is a step in which alkenyl carboxylic acid is introduced by reacting acetyl of pregnenolone with an alcohol group protected with THP represented by formula 6 with triphenyl phosphonium bromide of the compound represented by formula 7. In this step, after the introduction of alkenyl carboxylic acid, alkylation is immediately performed using alkyl halide without undergoing a separate purification process. The O-alkylation using alkyl halide can be performed by an informed method.

Step 2 is a step of deprotecting the THP protecting group of the compound represented by formula 10. The deprotection method can be performed by an informed method capable of removing THP, and as an example, the reaction can be performed under acid conditions.

The detailed description of step 3 is the same as the description of the preparation method of reaction formula 1.

In another aspect of the present invention, the present invention provides a mass production method of a novel vascular leakage blocker represented by formula 1 comprising a step of performing the preparation method of reaction formula 1 or the preparation method of reaction formula 3.

The preparation method of the present invention is easy to react and more productive and economical than the conventional method by using an intermediate that can easily remove impurities generated during the reaction. In addition, the preparation method can produce a novel vascular leakage blocker with a high yield by using a new reagent that has not been previously used in the step of generating an isomer, and is very advantageous in producing a high-quality active pharmaceutical ingredient.

In another aspect of the present invention, the present invention provides a compound represented by formula 4, which is an intermediate produced in the process of preparing the compound represented by formula 1.

[Formula 4]

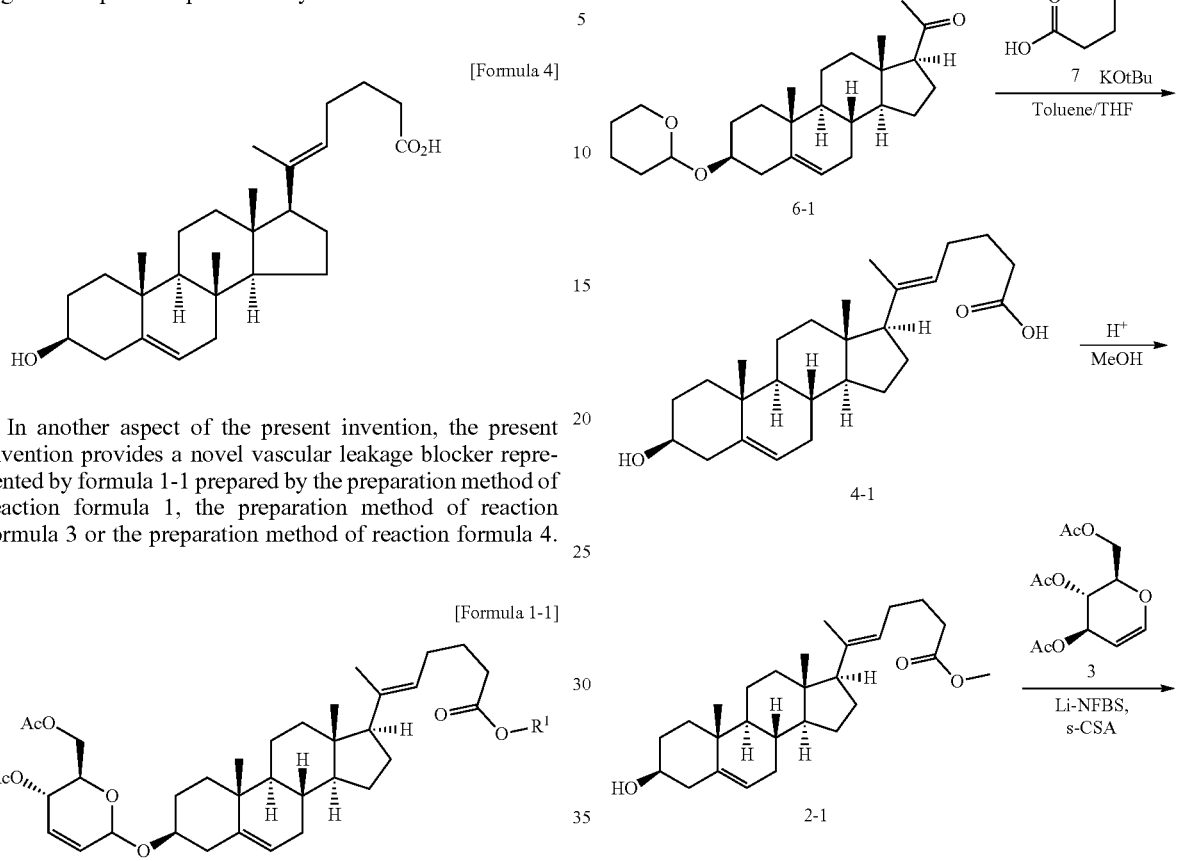

In another aspect of the present invention, the present invention provides a novel vascular leakage blocker represented by formula 1-1 prepared by the preparation method of reaction formula 1, the preparation method of reaction formula 3 or the preparation method of reaction formula 4.

[Formula 1-1]

Hereinafter, the present invention will be described in detail by the following examples and experimental examples.

However, the following examples and experimental examples are only for illustrating the present invention, and the contents of the present invention are not limited thereto.

Example 1: Preparation of a Novel Vascular Leakage Blocker 1

A novel vascular leakage blocker represented by formula 1-1 was prepared according to the preparation procedure shown in reaction formula A below.

[Reaction Formula A]

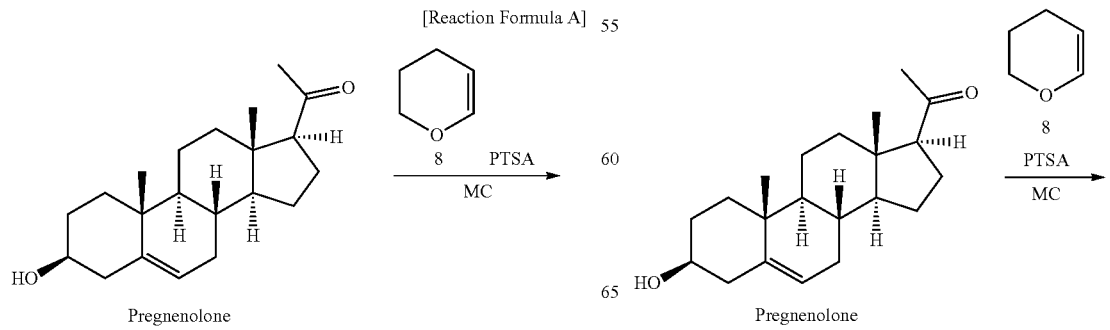

Step 1: Preparation of a Compound Represented by Formula 6-1

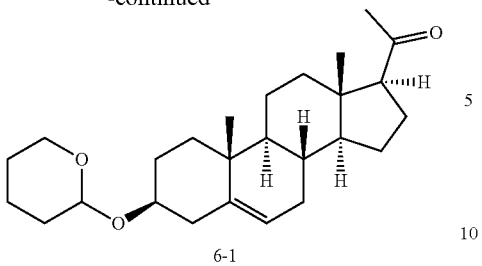

6-1

A thermometer was installed in a 5 L flask, to which 2000 mL of dichloromethane containing 200 g (0.632 mol) of pregnenolone and 113 mL (1.896 mol) of 3,4-dihydro-2H-pyran were added. The temperature was lowered to 0-5° C., and 3.0 g (15.8 mmol) of p-toluenesulfonic acid monohydrate was dissolved in 50 mL of tetrahydrofuran (THF), which was added dropwise to the mixture, followed by stirring at 0° C. for 1.5 hours. 800 mL of saturated sodium bicarbonate aqueous solution and 10 mL of triethylamine (TEA) were added to the reaction mixture at 0° C., followed by stirring. After separating the layers, the organic layer was washed with 800 mL of brine, and the aqueous layers were extracted again with 200 mL of dichloromethane, combined with the organic layer, dried and filtered with 200 g of anhydrous sodium sulfate, and distilled under reduced pressure. 1000 mL of MeOH and 5 mL of TEA were added to the obtained residue, heated to completely dissolve, and the temperature was lowered, followed by stirring at −5° C. for 1 hour. After adding 1000 mL of MeOH and 5 mL of TEA to the obtained residue, the mixture was heated to completely dissolve, and the temperature was lowered, followed by stirring at −5° C. for 1 hour. The resulting solid was filtered and washed with 200 mL of MeOH. As a result, 232.0 g (0.579 mol) of THP-pregnenolone represented by formula 6-1 was obtained as a pure white solid (yield: 91.6%).

$^1$H-NMR (400 MHz, CDCl$_3$): δ 5.33-5.36 (m, 1H), 4.71-4.72 (m, 1H), 3.85-3.94 (m, 1H), 3.46-3.56 (m, 2H), 1.00-2.55 (m, 32H), 0.62 (s, 3H).

Step 2: Preparation of a Compound Represented by Formula 4-1

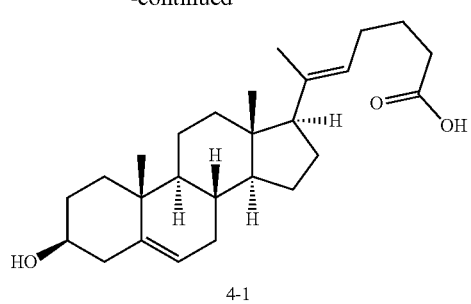

4-1

After installing a condenser, a heating mantle, and a mechanical stirrer in a 5 L reactor, the external temperature was heated to 119° C., and then cooled and dried while flowing nitrogen for 5 minutes. After adding 332.5 g (0.75 mol) of 4-(carboxybutyl)triphenyl phosphonium bromide and 168.1 g (1.50 mol) of potassium t-butoxide, 2000 mL of anhydrous toluene and 750 mL of anhydrous tetrahydrofuran were added thereto, followed by stirring for about 2 hours while heating at 119° C. (external temperature, internal state: mild reflux).

100.0 g (0.250 mol) of the compound represented by formula 6-1 (THP-pregnenolone) prepared in step 1 was dissolved in 500 mL of anhydrous toluene, which was added to the reaction solution, followed by reaction for about 20 hours. Upon completion of the reaction, the reaction solution was cooled to room temperature, and the reaction solvent was removed by distillation under reduced pressure, followed by vacuum drying for one hour. After 3000 mL of acetonitrile was added, 82.5 mL of hydrochloric acid and 62.5 mL of water were mixed and added thereto, followed by stirring at room temperature for 18 hours and filtering. The filtered solid was washed with 250 mL of ethyl acetate and 500 mL of hexane in that order, followed by vacuum drying. As a result, 200.0 g of the crude compound represented by formula 4-1 was obtained as a white solid.

$^1$H NMR (DMSO-dF, 400 MHz): δ(ppm) 11.97 (s, 1H), 5.27 (d, J=4.80 Hz, 1H), 5.16 (t, J=7.00 Hz, 1H), 4.60 (d, J=4.56 Hz, 1H), 3.27 (m, 1H), 2.21-0.88 (m, 32H), 0.52 (s, 3H).

Step 3: Preparation of a Compound Represented by Formula 2-1

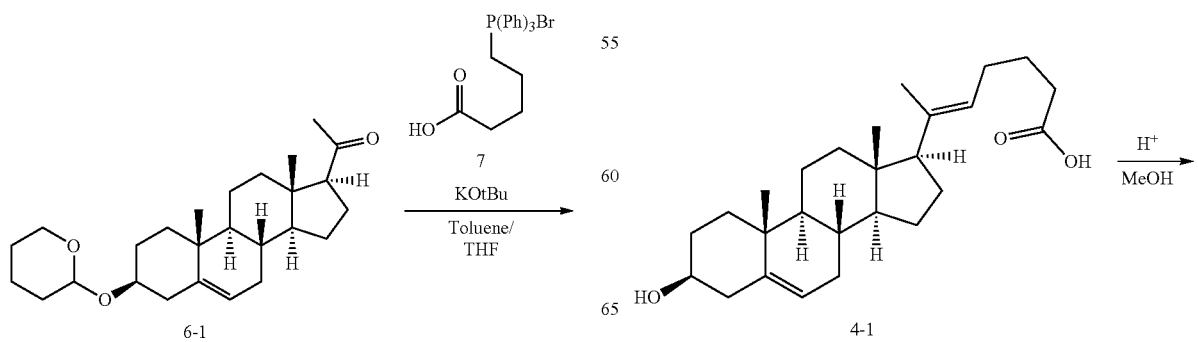

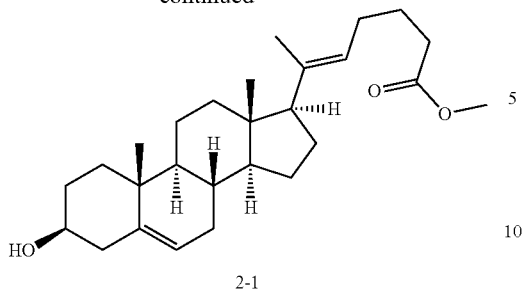

2-1

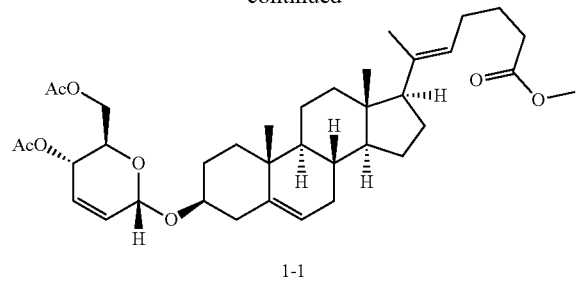

1-1

A thermometer was installed in a 2 L flask, to which 1000 mL of methanol containing 200 g (0.250 mol) of the crude compound represented by formula 4-1 obtained in step 2 and 4 mL (0.0075 mol) of sulfuric acid was added, followed by stirring at 80° C. for 3 hours. (The progress of the reaction was confirmed by TLC.)

Upon completion of the reaction, the reaction solution was concentrated under reduced pressure to remove methanol, and 200 ml of sodium bicarbonate aqueous solution and 800 ml of water were added thereto, followed by extraction with 1000 ml of ethyl acetate. The organic layer was washed twice with 1000 mL of water and 1000 mL of brine, dried over 30 g of anhydrous magnesium sulfate, filtered, and distilled under reduced pressure.

The obtained residue was dried in vacuo to completely remove the organic solvent, and dissolved in 750 mL of methanol by heating, followed by stirring at room temperature. When a solid was formed, the mixture was stirred at 0° C. for 1 hour, filtered, washed with 100 mL of −10° C. methanol and vacuum dried. As a result, 51.0 g (0.123 mol) of a compound represented by formula 2-1 was obtained as a white solid (2 steps from the compound of 6-1) (yield: 49.2%).

$^1$H-NMR (400 MHz, CDCl$_3$): δ 5.33-5.35 (m, 1H), 5.12-5.16 (m, 1H), 3.66 (s, 3H), 3.50-3.52 (m, 1H), 0.98-2.32 (m, 33H), 0.53 (s, 3H).

Step 4: Preparation of a Compound Represented by Formula 1-1

After installing a thermometer and a water bath in a 3 L flask, 100 g (0.241 mol) of the compound represented by formula 2-1 obtained in step 3 and 83.7 g (0.301 mol) of tri-O-acetyl D-glucal were dissolved in 300 mL of toluene and 600 mL of acetonitrile, and the mixture was added to the flask. While maintaining the temperature at 30-35° C., 9.22 g (0.030 mol) of lithium nonafluoro-1-butylsulfonate (Li—NFBS) and 0.28 g (0.00121 mol) of (s)-camphor sulfonic acid were added thereto, followed by stirring for 2 hours. Upon completion of the reaction, the reaction was quenched with 1200 ml of saturated sodium bicarbonate aqueous solution, followed by extraction with 1500 ml of petroleum ether. The organic layer was washed with 1200 ml of saturated sodium bicarbonate aqueous solution twice and 1200 ml of brine in that order, and the aqueous layers were extracted again with 200 ml of toluene/petroleum ether (1/5). The extract was combined with the organic layer, to which 100 g of anhydrous sodium sulfate and 10 g of charcoal were added, followed by stirring for an hour. The reactant was filtered using 40 g of celite and washed with 300 mL of toluene/petroleum ether (1/5). The filtrate was concentrated and dried in vacuo to give 102.9 g of the compound represented by formula 1-1 (yield: 68.1%).

$^1$H-NMR (400 MHz, CDCl$_3$): δ 5.79-5.88 (m, 2H), 5.35-5.36 (m, 1H), 5.27-5.29 (m, 1H), 5.12-5.16 (m, 2H), 4.15-4.24 (m, 3H), 3.66 (s, 3H), 3.54-3.57 (m, 1H), 0.91-2.32 (m, 38H), 0.54 (s, 3H).

Example 2: Preparation of a Novel Vascular Leakage Blocker 2

A novel vascular leakage blocker represented by formula 1-1 was prepared according to the preparation procedure shown in reaction formula B below.

[Reaction Formula B]

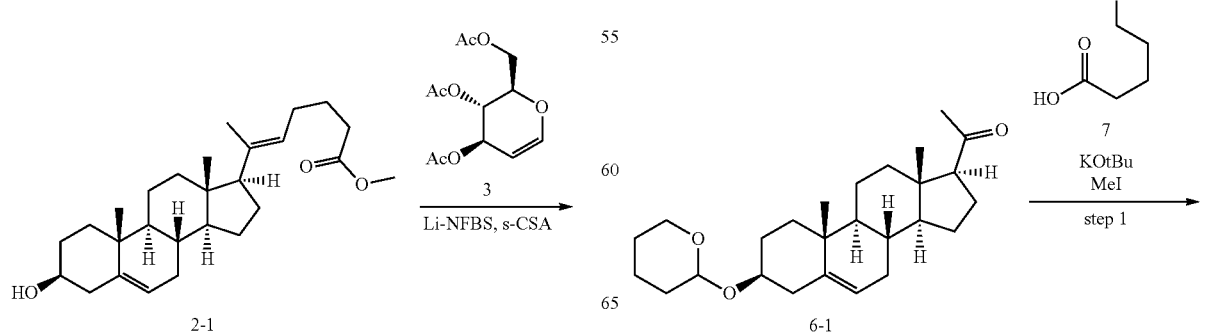

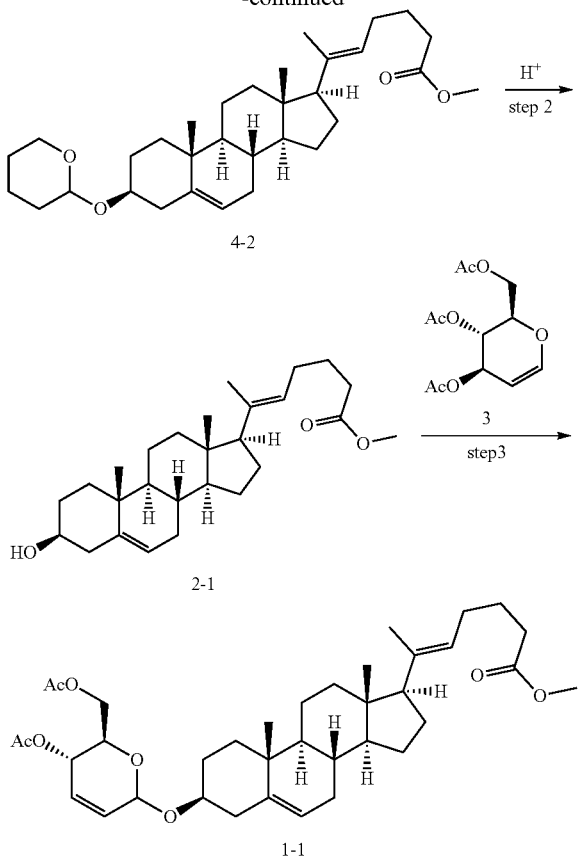

Step 1: Preparation of a Compound Represented by Formula 4-2

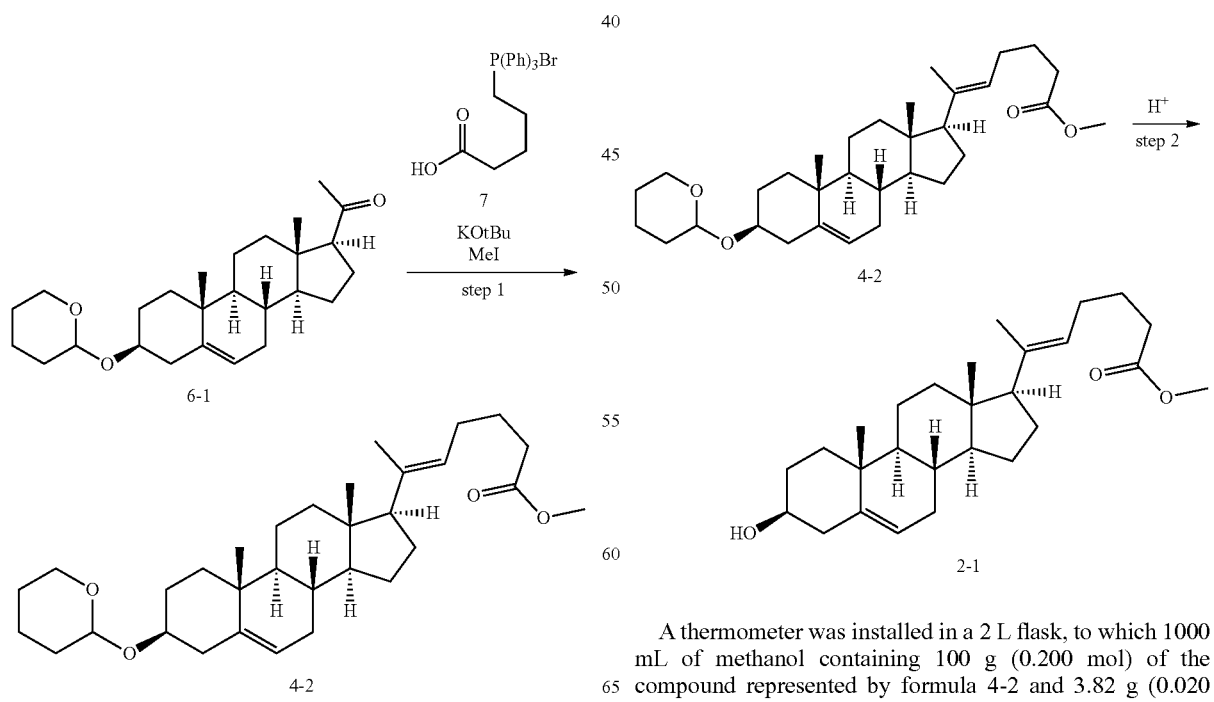

After installing a condenser, a heating mantle, and a mechanical stirrer in a 5 L reactor, the external temperature was heated to 119° C., and then cooled and dried while flowing nitrogen for 5 minutes. After adding 332.5 g (0.75 mol) of 4-(carboxybutyl)triphenyl phosphonium bromide and 168.1 g (1.50 mol) of potassium t-butoxide, 2000 mL of anhydrous toluene and 750 mL of anhydrous tetrahydrofuran were added thereto, followed by stirring for about 2 hours while heating at 119° C. (external temperature, internal state: mild reflux).

100.0 g (0.250 mol) of the compound represented by formula 6-1 was dissolved in 500 mL of anhydrous toluene, which was added to the reaction solution, followed by reaction for about 20 hours. Upon completion of the reaction, the reaction mixture was cooled to room temperature. 320 ml (5.14 mol) of methyl iodide and 1000 ml of acetone were added to the reaction mixture, followed by stirring at room temperature for 15 hours. The reaction mixture was distilled under reduced pressure to remove most of the organic solvent, to which 1500 mL of ethyl acetate was added to dissolve, followed by washing with 1000 mL of saturated ammonium chloride aqueous solution. The organic layer was washed with 1000 mL of water twice and 1000 mL of brine, dried over 100 g of sodium sulfate, and concentrated by filtering with 80 g of celite.

The obtained residue was dissolved in 2000 mL of methanol, followed by stirring at $10^1$ for 13 hours and at 4-5° C. for 1 hour. The resulting solid was filtered, washed with 200 mL of methanol, and dried in vacuo to give 66.2 g of the compound represented by formula 4-2 as a white solid (yield: 53.2%).

$^1$H NMR (400 MHz, CDCl$_3$): δ 5.36 (t, J=5.80 Hz, 1H), 5.16 (t, J=7.00 Hz, 1H), 4.71 (m, 1H), 3.93 (m, 1H), 3.66 (s, 3H), 3.56 (m, 2H), 2.37-0.88 (m, 38H), 0.54 (s, 3H).

Step 2: Preparation of a Compound Represented by Formula 2-1

A thermometer was installed in a 2 L flask, to which 1000 mL of methanol containing 100 g (0.200 mol) of the compound represented by formula 4-2 and 3.82 g (0.020 mol) of p-toluenesulfonic acid monohydrate was added, followed by stirring at 60° C. for 3 hours.

Upon completion of the reaction, the reaction solution was stirred at room temperature. The resulting solid was stirred at room temperature for 30 minutes and at 10¹ for 1 hour, filtered, washed with 100 mL of cooled methanol, and dried in vacuo to give 61.2 g (0.150 mol) of the compound represented by formula 2-1 as a white solid (yield: 75.0%).

$^1$H-NMR (400 MHz, CDCl$_3$) δ 5.33-5.35 (m, 1H), 5.12-5.16 (m, 1H), 3.66 (s, 3H), 3.50-3.52 (m, 1H), 0.98-2.32 (m, 33H), 0.53 (s, 3H).

Step 3: Preparation of a Compound Represented by Formula 1-1

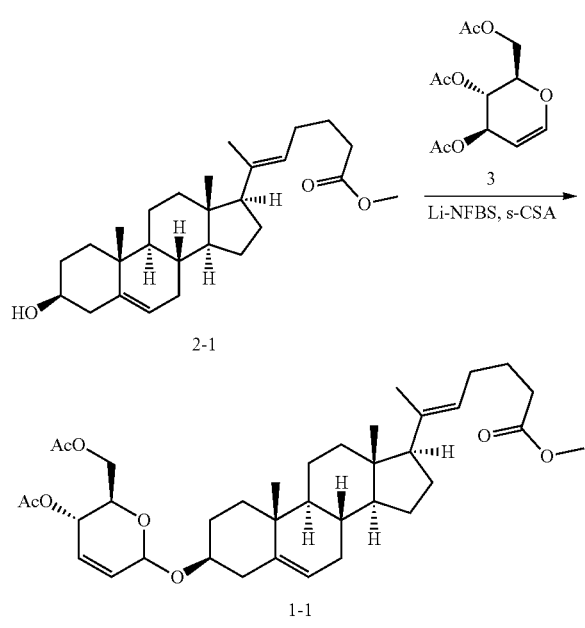

After installing a thermometer and a water bath in a 3 L flask, 100 g (0.241 mol) of the compound represented by formula 2-1 and 83.7 g (0.301 mol) of tri-O-acetyl D-glucal were dissolved in 300 mL of anhydrous toluene and 600 mL of acetonitrile, and the mixture was added to the flask. While maintaining the temperature at 30-35° C., 9.22 g (0.030 mol) of lithium nonafluoro-1-butylsulfonate and 0.28 g (0.00121 mol) of (s)-camphor sulfonic acid were added thereto, followed by stirring for 2 hours. Upon completion of the reaction, the reaction was quenched with 1200 ml of saturated sodium bicarbonate aqueous solution, followed by extraction with 1500 ml of petroleum ether. The organic layer was washed with 1200 ml of saturated sodium bicarbonate aqueous solution twice and 1200 ml of brine in that order, and the aqueous layers were extracted again with 200 ml of toluene/petroleum ether (1/5). The organic layer was dried over 100 g of anhydrous sodium sulfate, filtered using 40 g of celite, and washed with 300 mL of toluene/petroleum ether (1/5). The filtrate was concentrated and dried in vacuo to give 102.9 g of the compound represented by formula 1-1 (yield: 68.2%).

$^1$H-NMR (400 MHz, CDCl$_3$): δ 5.79-5.88 (m, 2H), 5.35-5.36 (m, 1H), 5.27-5.29 (m, 1H), 5.12-5.16 (m, 2H), 4.15-4.24 (m, 3H), 3.66 (s, 3H), 3.54-3.57 (m, 1H), 0.91-2.32 (m, 38H), 0.54 (s, 3H).

Experimental Example 1: Confirmation of Yield According to Scale Up

In order to confirm whether the preparation method of Example 1 was applicable to the mass production process, the yield of each step was evaluated by adjusting the manufacturing amount to a scale of 100 g or more. In addition, the yield above was compared with the yield of the preparation method of reaction formula 12 of Korean Patent Publication No. 10-2011-0047170, which discloses a chemical synthesis method for the same compound.

The differences between the preparation method of the present invention and the method of reaction formula 12 of Korean Patent Publication No. 10-2011-0047170 are as follows.

Manufacturing order: In the present invention, an ester compound was produced by selectively introducing alkyl only to carboxylic acid of an alcohol-carboxylic acid intermediate from which THP was removed in the presence of sulfuric acid, and tri-O-acetyl D-glucal was introduced using Li—NFBS.

In Korean Patent Publication No. 10-2011-0047170, an ester compound was produced by introducing alkyl to carboxylic acid using tritylsilyldiazomethane in the state where TTHP was bound, THP was removed in the presence of p-toluenesulfonic acid, and then tri-O-acetyl D-glucal was introduced in the presence of borontrifluoride diethyletherate.

The experimental results of each step of Example 1 according to the present invention and the step-by-step yields of the preparation method of reaction formula 12 of Korean Patent Publication No. 10-2011-0047170 are summarized and shown in Table 1 below.

TABLE 1

|  | Korean Patent Publication No. 10-2011-0047170 | Present Invention |  |
|---|---|---|---|
| Step 1 | Yield: 63.6% | Yield: 91.6% | Yield was improved by 28.0%. TEA was used as a stabilizer. |
| Step 2 | Yield: 65% | Yield: crude | Separation and purification were performed with a new intermediate different from the conventional method. |
| Step 3-1 | Yield: 70% | Yield: (step 2-3) | An intermediate different from the conventional method was used. The two-step reaction was reduced to the one-step reaction. The use of expensive reagents was avoided. Yield was improved by 10.5%. (step 2-3) |
| Step 3-2 | Yield: 85% | | |
| Step 4 | Yield: 56% | Yield: 68.2% | Li-NFBS, which has not been previously used, was used. Yield was improved by 12.2%. |
| Overall Yield | Yield: 13.7% | Yield: 32.5% | Yield was improved by 18.8%. |

As shown in Table 1, the overall yield (the overall yield of the preparation process) was improved to 32.5% in the present invention, compared to 13.7% in Korean Patent Publication No. 10-2011-0047170. Considering that the process in the present invention was a large scale of g level, and the process in Korean Patent Publication No. 10-2011-0047170 was a small scale of mg level, and that the yield usually decreases when the preparation process of a compound is scaled up from the mg scale to the g scale, the improvement of the yield was remarkably increased. In particular, the preparation method of the present invention simplified the preparation step by using a new intermediate in the preparation process and exhibited a high yield even in large scale manufacturing by varying the reagents used in each step and the purification method, so that the preparation method of the present invention can produce a novel vascular leakage blocker with a high yield, and can be economically and efficiently applied to mass production of drugs.

Therefore, the preparation method of the present invention is easy to react and more productive and economical than the conventional method by using an intermediate that can easily remove impurities generated during the reaction. In addition, the preparation method of the present invention can produce a novel vascular leakage blocker with a high yield by using a new reagent that has not been previously used in the step of generating an isomer, and is very advantageous in producing a high-quality active pharmaceutical ingredient.

INDUSTRIAL APPLICABILITY

The preparation method of the present invention is easy to react and more productive and economical than the conventional method by using an intermediate that can easily remove impurities generated during the reaction. In addition, the preparation method of the present invention can produce a novel vascular leakage blocker with a high yield by using a new reagent that has not been previously used in the step of generating an isomer, and is very advantageous in producing a high-quality active pharmaceutical ingredient.

What is claimed is:

1. A preparation method of a novel vascular leakage blocker represented by formula 1 comprising the following steps, as shown in reaction formula 1 below:
   preparing a compound represented by formula 2 by reacting a compound represented by formula 4 with a compound represented by formula 5 (step 1); and
   preparing a compound represented by formula 1 by reacting the compound represented by formula 2 obtained in step 1 above with a compound represented by formula 3 in the presence of a catalyst comprising lithium nonafluoro-1-butyl sulfonate (Li—NFBS) and (s)-camphor sulfonic acid (step 2):

[Reaction Formula 1]

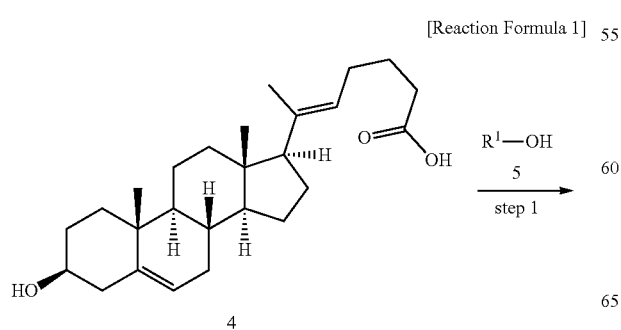

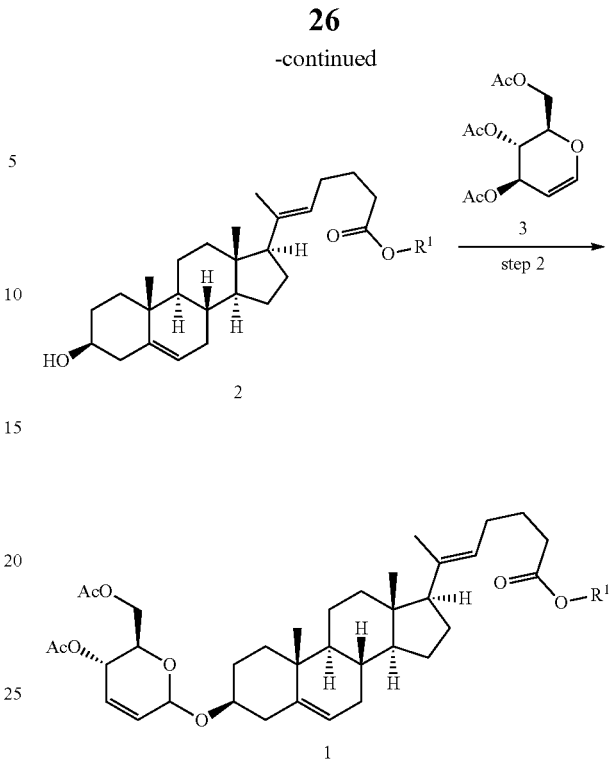

In reaction formula 1, $R^1$ is straight or branched $C_{1-10}$ alkyl.

2. The preparation method of a novel vascular leakage blocker represented by formula 1 according to claim 1, wherein the compound represented by formula 2 of step 1 is purified by recrystallization.

3. The preparation method of a novel vascular leakage blocker represented by formula 1 according to claim 2, wherein the recrystallization of step 1 is performed using any one selected from the group consisting of methanol, ethanol, toluene, ethyl acetate, acetonitrile and petroleum ether, or a mixed solvent thereof as a recrystallization solvent.

4. The preparation method of a novel vascular leakage blocker represented by formula 1 according to claim 1, wherein the catalyst is one or more of cation perfluoro-1-alkylsulfonate, (s)-camphor sulfonic acid, iodine, Amberlyst 15 and borontrifluoride etherate.

5. The preparation method of a novel vascular leakage blocker represented by formula 1 according to claim 4, wherein the cation is lithium, sodium, potassium or cesium, and the alkyl is straight or branched perfluoro $C_{1-10}$ alkyl.

6. The preparation method of a novel vascular leakage blocker represented by formula 1 according to claim 1, wherein the preparation method further comprises the step of preparing a compound represented by formula 4 by reacting a compound represented by formula 6 with a compound represented by formula 7 and then treating it under acid condition, as shown in reaction formula 2 below:

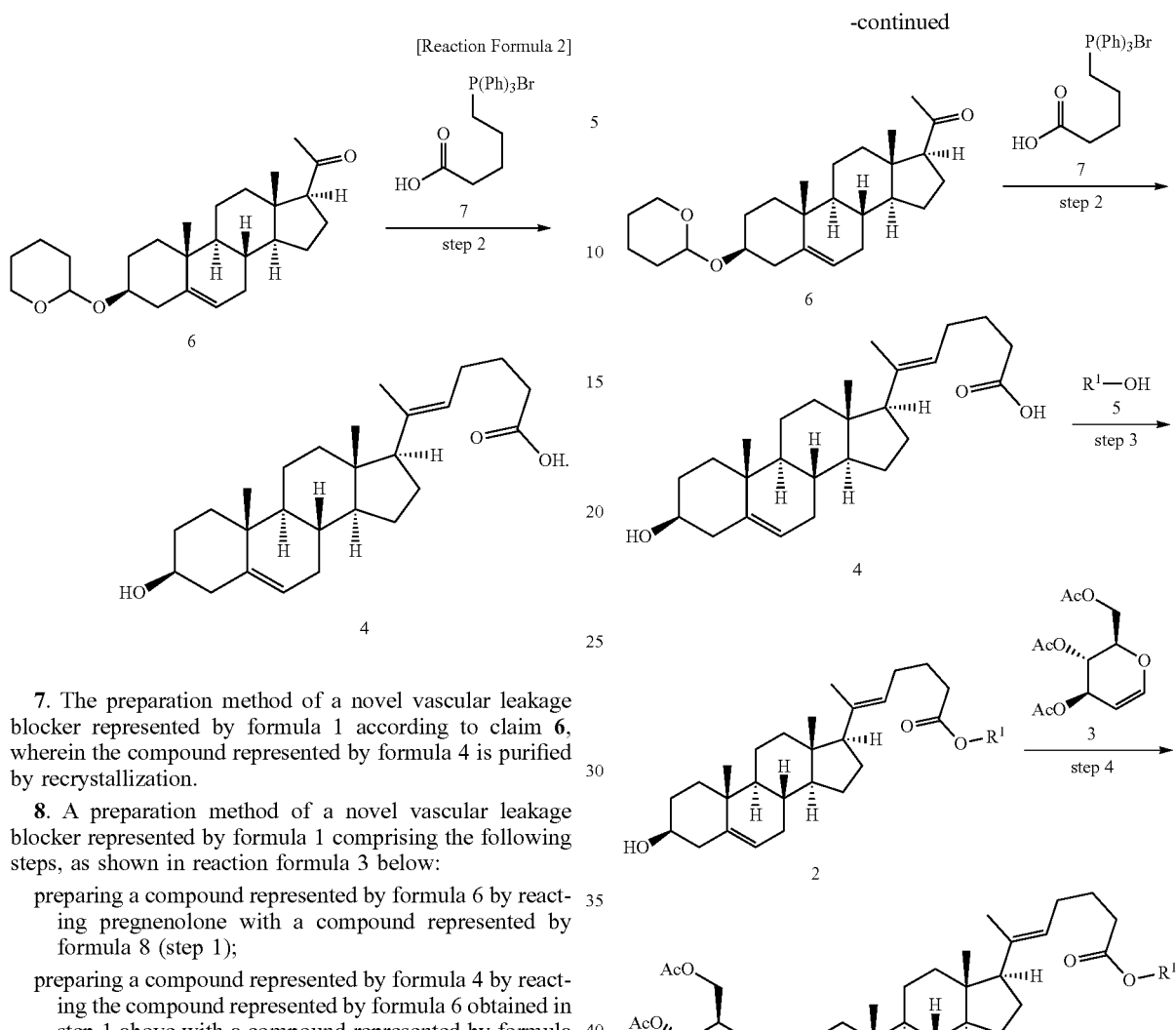

7. The preparation method of a novel vascular leakage blocker represented by formula 1 according to claim 6, wherein the compound represented by formula 4 is purified by recrystallization.

8. A preparation method of a novel vascular leakage blocker represented by formula 1 comprising the following steps, as shown in reaction formula 3 below:
preparing a compound represented by formula 6 by reacting pregnenolone with a compound represented by formula 8 (step 1);
preparing a compound represented by formula 4 by reacting the compound represented by formula 6 obtained in step 1 above with a compound represented by formula 7 and then treating it under acid condition (step 2);
preparing a compound represented by formula 2 by reacting the compound represented by formula 4 obtained in step 2 above with a compound represented by formula 5 (step 3); and
preparing a compound represented by formula 1 by reacting the compound represented by formula 2 obtained in step 3 above with a compound represented by formula 3 in the presence of a catalyst comprising lithium nonafluoro-1-butyl sulfonate (Li—NFBS) and (s)-camphor sulfonic acid (step 4):

[Reaction Formula 3]

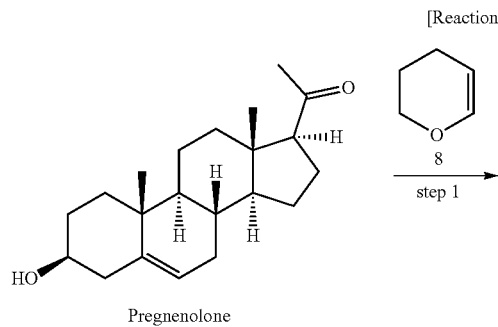

In reaction formula 3,
$R^1$ is straight or branched $C_{1-10}$ alkyl.

9. The preparation method of a novel vascular leakage blocker represented by formula 1 according to claim 8, wherein triethylamine (TEA) is added in the step 1.

10. The preparation method of a novel vascular leakage blocker represented by formula 1 according to claim 8, wherein the compound represented by formula 6 of step 1, the compound represented by formula 4 of step 2 or the compound represented by formula 2 of step 3 is purified by recrystallization.

11. The preparation method of a novel vascular leakage blocker represented by formula 1 according to claim 10, wherein the recrystallization is performed using one or more selected from the group consisting of methanol, ethanol, toluene, ethyl acetate, acetonitrile and petroleum ether, or a mixed solvent thereof as a recrystallization solvent.

12. A preparation method of a novel vascular leakage blocker represented by formula 1 comprising the following steps, as shown in reaction formula 4 below:
preparing a compound represented by formula 10 by reacting a compound represented by formula 6, a compound represented by formula 7 and a compound represented by formula 9 (step 1);

preparing a compound represented by formula 2 by reacting the compound represented by formula 10 obtained in step 1 above with an acid material (step 2); and preparing a compound represented by formula 1 by reacting the compound represented by formula 2 obtained in step 2 above with a compound represented by formula 3 in the presence of a catalyst comprising lithium nonafluoro-1-butyl sulfonate (Li—NFBS) and (s)-camphor sulfonic acid (step 3):

[Reaction Formula 4]

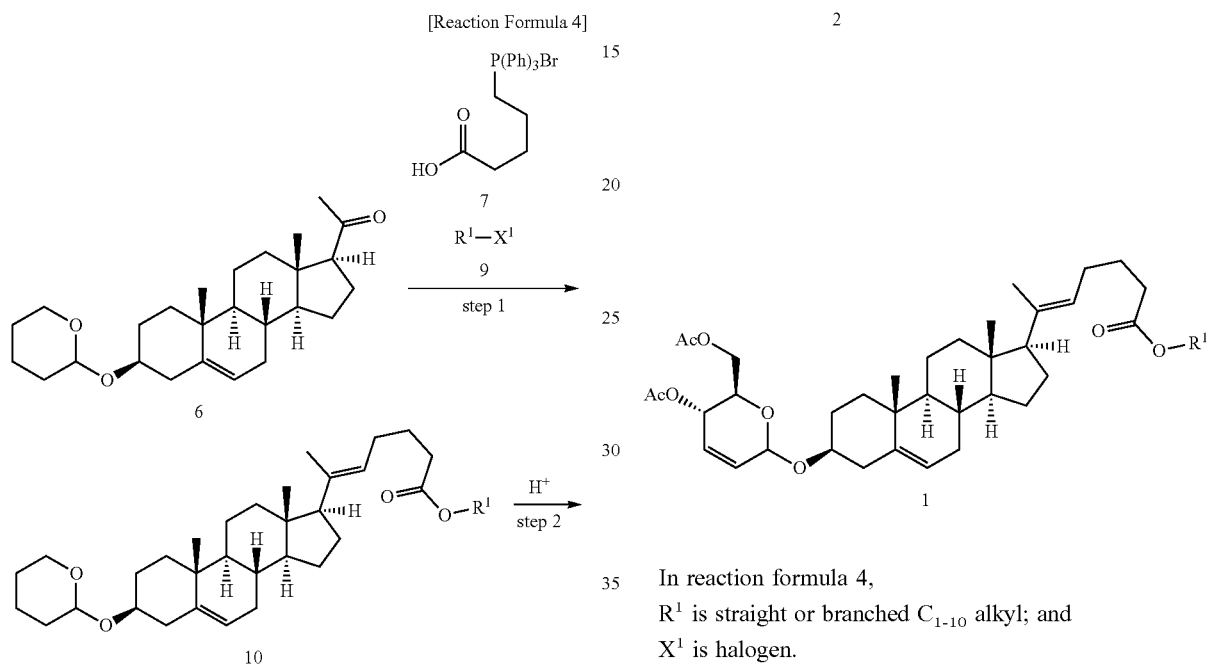

In reaction formula 4, $R^1$ is straight or branched $C_{1-10}$ alkyl; and $X^1$ is halogen.

* * * * *